(12) United States Patent
Zink et al.

(10) Patent No.: US 6,358,496 B1
(45) Date of Patent: Mar. 19, 2002

(54) INDOLIN DERIVATIVES AS SUN PROTECTION AGENTS

(75) Inventors: Rudolf Zink, Therwil (CH); Helmut Luther, Grenzach-Wyhlen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/806,349
(22) PCT Filed: Sep. 21, 1999
(86) PCT No.: PCT/EP99/06984
§ 371 Date: Mar. 19, 2001
§ 102(e) Date: Mar. 19, 2001
(87) PCT Pub. No.: WO00/20388
PCT Pub. Date: Apr. 13, 2000

(30) Foreign Application Priority Data

Oct. 2, 1998 (EP) .............................. 98810993

(51) Int. Cl.⁷ .............................. A61K 7/42; A61K 7/44; A61K 7/00; A61K 31/53; A61K 31/40
(52) U.S. Cl. .......................... 424/59; 424/60; 424/400; 424/401; 514/245; 514/419
(58) Field of Search ............................ 424/59, 60, 400, 424/401; 514/419, 245

(56) References Cited

U.S. PATENT DOCUMENTS

| | | | |
|---|---|---|---|
| 3,925,015 A | 12/1975 | Kuhlthau | |
| 4,522,808 A | 6/1985 | Jaquet et al. | |
| 4,889,410 A | 12/1989 | Elwood | |

FOREIGN PATENT DOCUMENTS

| | | |
|---|---|---|
| DE | 19539623 | 9/1970 |
| DE | 2152948 | 4/1973 |
| GB | 929394 | 6/1963 |

OTHER PUBLICATIONS

Chem. Abstr. vol. 121, No. 16, abstract No. 191470c, (1994) for JP 05305773.
Chem. Abstr. vol. 115, No. 20, abstract No. 210209u, (1991) for JP 03134063.
Chem. Abstr. vol. 118, No. 25, abstract No. 255031h, (1993) for G.V. Ratovskii et al., Zh. Obshch. Khim., vol. 62, No. 9, (1992), pp. 2046–2051.
Chem. Abstr. vol. 97, No. 10, abstract No. 73922q, (1982), for JP 82030760.

*Primary Examiner*—Shelley A. Dodson
(74) *Attorney, Agent, or Firm*—Kevin T. Mansfield

(57) ABSTRACT

There is described the use of indoline derivatives of formula

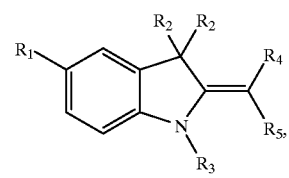
(1)

wherein
$R_1$ is hydrogen; $C_1-C_5$alkyl; $C_1-C_{18}$alkoxy; or halogen;
$R_2$ is $C_1-C_8$alkyl; $C_5-C_7$cycloalkyl; $C_6-C_{10}$aryl;
$R_3$ is $C_1-C_{18}$alkyl or a radical of formula

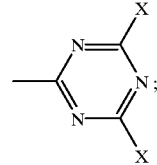
(1a)

$R_4$ is hydrogen; or a radical of formula

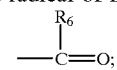

$R_5$ is

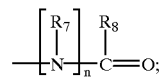

$C_1-C_{18}$alkoxy; or a radical of formula

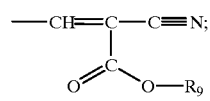
(1b)

$R_6$ and $R_7$ are each independently of the other hydrogen; or $C_1-C_5$alkyl;
$R_8$ is hydrogen; $C_1-C_5$alkyl; $C_5-C_7$cycloalkyl; phenyl; phenyl-$C_1-C_3$alkyl;
$R_9$ is $C_1-C_{18}$alkyl;
X is halogen; a radical of formula

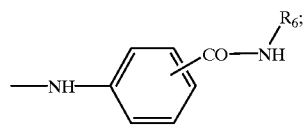
(1c)

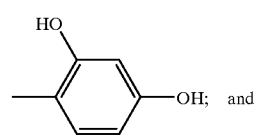

(1d)

and n is 0; or 1,
as light-protective agents.

11 Claims, No Drawings

INDOLIN DERIVATIVES AS SUN PROTECTION AGENTS

The present invention relates to indoline derivatives and to the use of those compounds as light-protective agents.

Indoline compounds are known from dye chemistry, where they are used as intermediates or starting materials. Indoxyl, for example, occurs as an intermediate in industrial indigo synthesis. Trimethyl-2-methyleneindoline (Fischer base) is used as starting compound in the preparation of polymethine dyes.

It has been found, surprisingly, that certain indoline derivatives are also suitable as light-protective agents.

The present invention accordingly relates to the use of indoline derivatives of formula

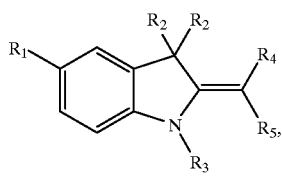

(1)

wherein $R_1$ is hydrogen; $C_1$–$C_5$alkoxy; $C_1$–$C_{18}$alkoxy; or halogen;

$R_2$ is $C_1$–$C_8$alkyl; $C_5$–$C_7$cycloalkyl; $C_6$–$C_{10}$aryl;

$R_3$ is $C_1$–$C_{18}$alkyl; or a radical of formula (1a)

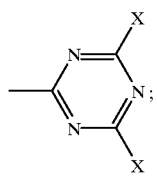

(1a)

$R_4$ is hydrogen; or a radical of formula (1b)

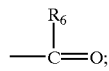

(1b)

$R_5$ is a radical of formula (1c)

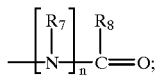

(1c)

$C_1$–$C_{18}$alkoxy; or a radical of formula

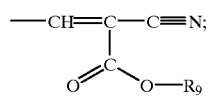

(1d)

$R_6$ and $R_7$ are each independently of the other hydrogen; or $C_1$–$C_5$alkyl;

$R_8$ is hydrogen; $C_1$–$C_5$alkyl; $C_5$–$C_7$cycloalkyl; phenyl; phenyl-$C_1$–$C_3$alkyl;

$R_9$ is $C_1$–$C_{18}$alkyl;

X is halogen; a radical of formula (1e)

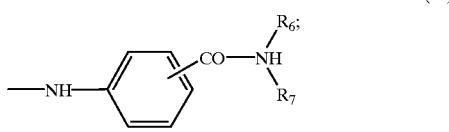

(1e)

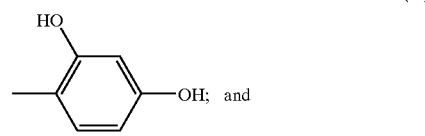

(1f)

n is 0; or 1, as light-protective agents.

$C_1$–$C_{18}$Alkyl denotes straight-chain or branched alkyl radicals, for example methyl, ethyl, n-propyl, isopropyl, n-butyl, sec-butyl, tert-butyl, amyl, isoamyl or tert-amyl, hexyl, heptyl, octyl, isooctyl, nonyl, decyl, undecyl, dodecyl, tetradecyl, pentadecyl, hexadecyl, heptadecyl or octadecyl.

$C_1$–$C_{18}$Alkoxy is, for example, methoxy, ethoxy, n-propoxy, isopropoxy, n-butoxy, sec-butoxy, tert-butoxy, amyloxy, isoamyloxy or tert-amyloxy, hexyloxy, heptyloxy, octyloxy, isooctyloxy, nonyloxy, decyloxy, undecyloxy, dodecyloxy, tetradecyloxy, pentadecyloxy, hexadecyloxy, heptadecyloxy or octadecyloxy.

Halogen is fluorine or bromine, and especially chlorine.

$C_5$–$C_7$Cycloalkyl is, for example, cyclopentyl, cycloheptyl and especially cyclohexyl.

$C_6$–$C_{10}$Aryl is phenyl or naphthyl.

Preference is given according to the invention to the use of compounds of formula (1) wherein

(1g)

$R_5$ is a radical of formula (1g)

and $R_8$ is hydrogen; $C_1$–$C_5$alkyl; or phenyl, especially hydrogen or methyl.

Also of interest are compounds of formula (1) wherein $R_5$ is $C_1$–$C_{18}$alkoxy, and especially a radical of formula

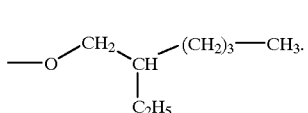

(1h)

Also of interest are compounds of formula (1) wherein $R_5$ is a radical of formula

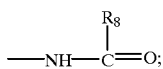

(1i)

and $R_8$ is hydrogen; or methyl.

Of special interest are also compounds of formula (1) wherein $R_3$ is $C_3$–$C_{18}$isoalkyl.

Exemplary compounds used in accordance with the invention correspond to formulae

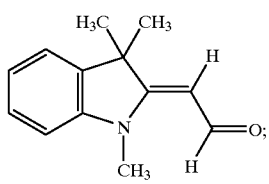

(2)

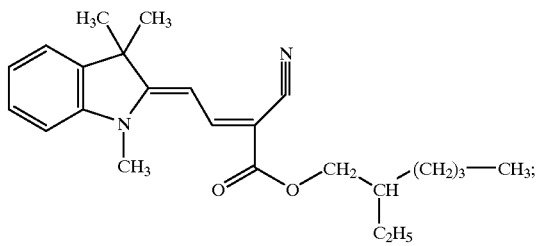

(3)

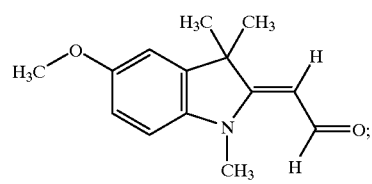

(4)

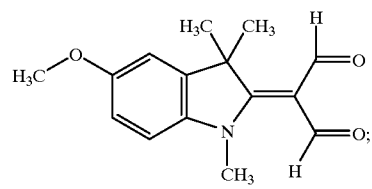

(5)

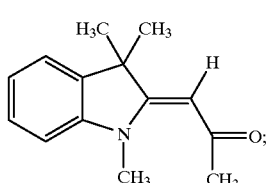

(6)

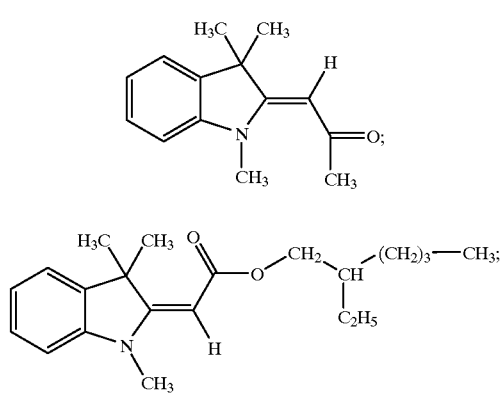

(7)

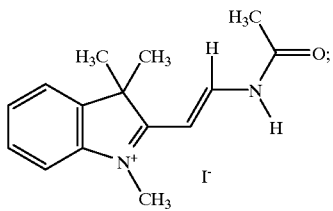

(8)

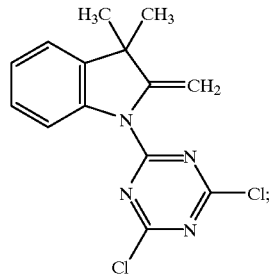

(9)

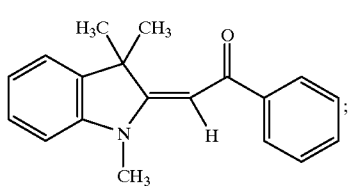

(10)

or

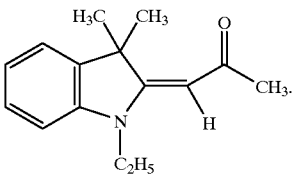

(11)

Some of the compounds of formulae (1) to (11) are known compounds while some are new compounds.

The new compounds correspond to formula

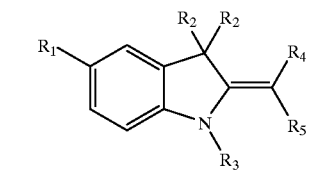

(12)

wherein $R_1$ is hydrogen; $C_1$–$C_5$alkyl; $C_1$–$C_5$alkoxy; or halogen;

$R_2$ is $C_1$–$C_5$alkyl; $C_5$–$C_7$cycloalkyl; $C_6$–$C_{10}$aryl;

$R_3$ is $C_1$–$C_5$alkyl or a radical of formula (1a)

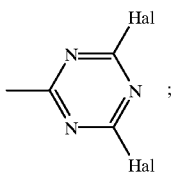

$R_4$ is hydrogen; or a radical of formula (1b)

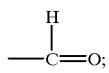

$R_5$ is $C_5$–$C_{18}$alkoxy; a radical of formula (1b); or a radical of formula

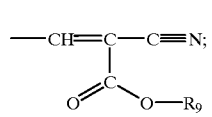

$R_9$ is $C_1$–$C_{18}$alkyl; or $R_4$ and $R_5$ denote a radical of formula (1b).

The indoline derivatives used in accordance with the invention are prepared in a manner known per se by means of condensation of the indoline compound (Fischer base) of formula

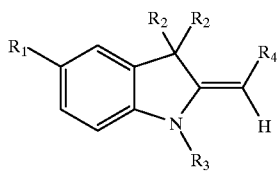

with the appropriate acid chloride or a CH acid compound to form the compound of formula (1).

The reaction is usually carried out at temperatures of from 20 to 110° C. in the presence of an inert solvent, for example petroleum ether, toluene, xylene, a mixture of xylene isomers, or of a halogenated hydrocarbon, for example $CH_2Cl_2$. The reaction can, however, also be performed without solvents. The reaction time is usually a few minutes and may last for up to a few hours.

The compounds of formula (1) are especially suitable as UV filters, that is to say for protecting ultraviolet-sensitive organic materials, especially the skin and hair of humans and animals, against the damaging action of UV radiation. The compounds are accordingly suitable as light-protective agents in cosmetic, pharmaceutical and veterinary-medicinal compositions. The compounds can be used both in dissolved form and in the micronised state.

The invention relates also to a cosmetic composition comprising a compound of formula (1).

For cosmetic use, these light-protective agents, unless they are water-soluble, usually have an average particle size in the range from 0.02 to 2, preferably from 0.05 to 1.5, and very especially from 0.1 to 1.0, m. The insoluble light-protective agents in accordance with the invention can be brought to the desired particle size by customary methods, e.g. grinding with, for example, a jet, ball, vibration or hammer mill. Preference is given to performing the grinding in the presence of from 0.1 to 30% by weight, preferably from 0.5 to 15% by weight, based on the UV absorber, of a grinding aid, for example an alkylated vinylpyrrolidone polymer, a vinylpyrrolidone-vinyl acetate copolymer, an acyl glutamate, an alkyl polyglucoside or, especially, a phospholipid.

The light-protective agents can also be used dry in powder form. For that purpose, the light-protective agents are subjected to known grinding processes such as vacuum atomisation, countercurrent spray-drying etc. Such powders have a particle size of from 0.1 nm to 2 µm. To avoid agglomeration processes, the light-protective agents can be coated, before the pulverisation process, with a surface-active compound, for example an anionic, non-ionic or amphoteric surfactant, for example with phospholipids or known polymers, such as PVP, acrylates etc.

The cosmetic composition, in addition to comprising the UV absorber according to the invention, may also comprise one or more further UV-protective substances of the following classes of substance;

1. p-aminobenzoic acid derivatives, e.g. 4-dimethylaminobenzoic acid 2-ethylhexyl ester;
2. salicylic acid derivatives, e.g. salicylic acid 2-ethylhexyl ester;
3. benzophenone derivatives, e.g. 2-hydroxy-4-methoxybenzophenone and the 5-sulfonic acid derivative thereof;
4. dibenzoylmethane derivatives, e.g. 1-(4-tert-butylphenyl)-3-(4-methoxyphenyl)propane-1,3-dione;
5. diphenyl acrylates, e.g. 2-ethylhexyl-2-cyano-3,3-diphenyl acrylate and 3-(benzo-furanyl)-2-cyanoacrylate;
6. 3-imidazol-4-yl-acrylic acid and esters;
7. benzofuran derivatives, especially 2-(p-aminophenyl) benzofuran derivatives, described in EP-A-582 189, U.S. Pat. Nos. 5,338,539, 5,518,713 and EP-A-613 893;
8. polymeric UV absorbers, e.g. the benzylidene malonate derivatives described in EP-A-709 080;
9. cinnamic acid derivatives, e.g. the 4-methoxycinnamic acid 2-ethylhexyl ester and isoamyl ester or cinnamic acid derivatives disclosed in U.S. Pat. No. 5,601,811 and WO 97/00851;
10. camphor derivatives, e.g. 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo [2.2.1 ]heptane-1-methanesulfonic acid) and salts, 3-(4'-sulfo)benzylidene-bornan-2-one and salts;
11. trianilino-s-triazine derivatives, e.g. 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;
12. 2-hydroxyphenylbenzotriazole derivatives;
13. 2-phenylbenzimidazole-5-sulfonic acid and salts thereof;
14. menthyl-o-aminobenzoate;
15. inorganic micropigments, for example $TiO_2$ (variously encapsulated);
16. N-substituted benzimidazoles, as described in EP-A-0 843 995;
17. hydroxyphenylbenzotriazoles and derivatives, especially siloxane derivatives;

18. siloxanes of oxanilide derivatives, as described in EP-A-0 712 856.

The UV absorbers described in "Sunscreens", Eds. N. J. Lowe, N. A. Shaath, Marcel Dekker, Inc., New York and Basle or in Cosmetics & Toiletries (107), 50ff (1992) can also be used as additional UV-protective substances in the formulation according to the invention.

Furthermore, the cosmetic composition according to the invention can also be used together with known antioxidants, for example amino acids (e.g. glycerol, histidine, tyrosine, tryptophan) and derivatives thereof, peptides (e.g. carnosine) and derivatives thereof, vitamin E and vitamin A and derivatives thereof, derivatives of vitamin C, carotenoids, flavanoids and derivatives thereof and ubiquinones or HALS (="Hindered Amine Light Stabilizers") compounds.

The cosmetic compositions contain from 0.1 to 15% by weight, preferably from 0.5 to 10% by weight, based on the total weight of the composition, of a light-protective agent of formula (1) or of a mixture of light-protective agents, and a cosmetically tolerable adjuvant.

The cosmetic compositions can be prepared by physically mixing the UV absorber(s) with the adjuvant using customary methods, for example by simply stirring the individual components together, especially by utilising the dissolution characteristics of known cosmetic UV absorbers, for example OMC, salicylic acid isooctyl ester, among others.

The cosmetic compositions may be formulated as a water-in-oil or oil-in-water emulsion, as an oil-in-alcohol lotion, as a vesicular dispersion of an ionic or non-ionic amphiphilic lipid, as a gel, a solid stick or as an aerosol formulation.

In the case of a water-in-oil or oil-in-water emulsion, the cosmetically tolerable adjuvant contains preferably from 5 to 50% of an oily phase, from 5 to 20% of an emulsifier and from 30 to 90% water. The oily phase may contain any oil suitable for cosmetic formulations, e.g. one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol. Di- or/and tri-valent metal salts (alkaline earth metal, $Al^{3+}$, among others) of one or more alkoxycarboxylic acids may also be used.

For the cosmetic compositions it is possible to use any conventionally used emulsifier, for example one or more ethoxylated esters of natural derivatives, e.g. polyethoxylated esters of hydrogenated castor oil; or silicone oil emulsifiers, e.g. silicone polyol; fatty acid soaps, which may or may not be ethoxylated; fatty alcohols or fatty acids and polyoxyethylene derivatives thereof; sorbitan esters, which may or may not be ethoxylated; ethoxylated fatty acids or fatty acid esters; or ethoxylated glycerides.

Further suitable emulsifiers are fatty acid partial esters of polyhydric alcohols such as glycol, 1,2-propylene glycol, glycerol, sorbitol and pentaerythritol, and also protein-fatty acid condensation products and lanolin derivatives, salts of alkylcarboxylic acids, of alkyl sulfates or sulfonates or of polyglycol ethers. Mixtures of anionic and non-ionic emulsifiers or mixtures of purely non-ionic surface-active substances having different HLB values may also be used. Mixtures of fatty alcohol and fatty acid polyglycol ethers or of oxethylated fats are also customary.

The cosmetic compositions may also comprise further components, e.g. emollients, emulsion stabilisers, skin humectants, skin-tanning accelerators, thickeners, e.g. xanthan, moisture-retaining agents, e.g. glycerol, preservatives, perfumes and colourings.

Cosmetic formulations according to the invention are contained in a variety of cosmetic preparations. Especially the following preparations, for example, come into consideration:

skin-care preparations, e.g. skin-washing and cleansing preparations in the form of tablet-form or liquid soaps, soapless detergents or washing pastes;

bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose and pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

intimate hygiene preparations, e.g. intimate washing lotions or intimate sprays;

foot-care preparations, e.g. foot baths, foot powders, foot creams or foot balsams, special deodorants and anti-perspirants or callus-removing preparations;

light-protective preparations, such as sun milks, lotions, creams and oils, sun blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. soapless detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or cream perfumes;

dental-care, denture-care and mouth-care preparations, e.g. toothpastes, gel toothpastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

The formulations mentioned may be presented in various forms, for example in the form of liquid preparations as a W/O, O/W, O/W/O, W/O/W or PIT emulsion or any kind of microemulsion, in the form of a gel, in the form of an oil, cream, milk or lotion, in the form of a powder, lacquer, tablet or make-up, in the form of a stick, in the form of a spray (propellant-gas spray or pump-action spray) or of an aerosol, in the form of a foam, or in the form of a paste.

The cosmetic formulations are distinguished by excellent protection of human skin against the damaging effect of sunlight.

In the following Examples percentages refer to weight. Amounts refer to the pure substance.

PREPARATION EXAMPLES

Example 1

10 g of 2-(1,3,3-trimethyl-indolin-2-ylene) acetaldehyde (=Fischer base aldehyde; technical grade) are dissolved in 250 ml of petroleum ether (boiling range 80–110° C.) under reflux. The solution is clarified by means of filtration using 1 g of filtration aid and, with stirring, slowly cooled; after 16 hours, it is filtered at 25° C. and dried. 6 g of pure, slightly yellow crystals of formula

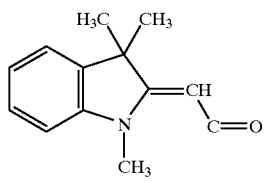

(101)

having a melting point of 105–106° C. are obtained.

$\epsilon=34520$ l/(mol/cm) in ethanol at $\lambda_{max.}=341$ nm:

photostability $t_{1/2}=208$ hours

Example 2

5 g of 2-(1,3,3-trimethyl-indolin-2-ylene)acetaldehyde (=Fischer base aldehyde) are dissolved in 50 ml of toluene. There are then added 5 drops of piperidine and 0.5 g of 100% acetic acid; 5 g of cyanoacetic acid 2-ethyl ester are added and heating is carried out at from 100 to 110° C. under reflux. That temperature is maintained for 3 hours and the water that forms is removed using a separator. Most of the toluene is then distilled off and the residue is dissolved in 80 ml of petroleum ether (boiling range 80–110° C.) in the hot state and clarified by filtration. On slow cooling, the compound of formula

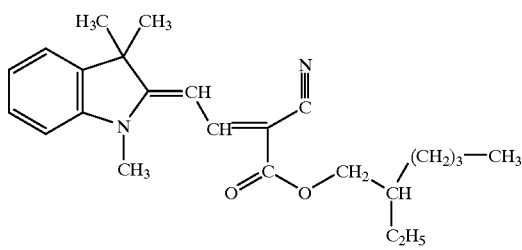

(102)

crystallises out and, at 25° C., is filtered off. After drying, 7.1 g of yellow crystals having a melting point of 75–77° C. are obtained.

$\epsilon=62081$ in ethanol l/(mol/cm) at $\lambda_{max}=434$ nm, elemental analysis for $C_{24}H_{32}N_2O_2$ [%]:

|  | C | H | N | O |
|---|---|---|---|---|
| calculated | 75.75 | 8.48 | 7.37 | 8.41 |
| found | 75.7 | 8.5 | 7.4 | 8.6 |

Example 3

17.3 g of 1,3,3-trimethyl-2-methylene-indoline (=Fischer base) are dissolved in 30 ml of methylene chloride and, over the course of half an hour, 14 g of benzoyl chloride are added dropwise at 20–32° C. The reaction mass is heated to 45° C. and that temperature is maintained for half an hour; the reaction mixture is cooled to 25° C. and the precipitated hydrochloride of the starting material is filtered off. The red filtrate is concentrated to dryness and recrystallised from a mixture of 30 ml of acetone/3 ml of water. 8.7 g of the compound of formula

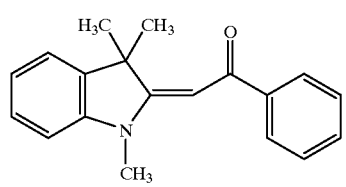

(103)

are thereby obtained in the form of pale yellow crystals having a melting point of 133–134° C.

$\epsilon=29427$ in dioxane l/(mol/cm) at $\lambda_{max}=377$ nm.

APPLICATION EXAMPLES

Example 4

Preparation of an O/W Lotion

| INCI name | % |
|---|---|
| polyglyceryl-3 methylglucose distearate | 3.0 |
| decyl oleate | 7.2 |
| isopropyl palmitate | 7.0 |
| caprylic/capric triglyceride | 8.4 |
| compound of formula (103) | 4.0 |

-continued

| INCI name | % |
|---|---|
| octyl methoxycinnamate | 5.0 |
| glycerol | 3.0 |
| phenoxyethanol & (methyl, ethyl, propyl, butyl) parabens | 0.5 |
| deionised water | 60.9 |
| carbomer | 0.2 |
| isopropyl palmitate | 0.8 |
| NaOH (10%) | as required |

The oil phase and the aqueous phase are separately heated to 75–80° C. and cautiously brought together. That is followed by intensive homogenisation and cooling to room temperature with gentle stirring.

Using an Optometrics SPF-290 Analyzer (2 $\mu$l/cm$^2$ on Transpore film) an in vitro SPF of 15 is determined. The Australian standard for UVA protection (Australian/New Zealand Standard, 15/NZS 2604: 1993) is met.

Example 5
Preparation of an O/W Emulsion

| | INCI name | % |
|---|---|---|
| A | polyglyceryl-3 methylglucose distearate | 2.5 |
| | decyl oleate | 7.7 |
| | isopropyl palmitate | 7.0 |
| | vitamin E acetate | 1.5 |
| | caprylic/capric triglyceride | 9.5 |
| | bis-octylphenol methoxyphenyl triazine | 3.0 |
| | compound of formula (101) | 3.5 |
| B | glycerol | 3.0 |
| | phenoxyethanol & (methyl, ethyl, propyl, butyl) parabens | 0.5 |
| | deionised water | 64.3 |
| C | carbomer | 0.2 |
| | isopropyl palmitate | 0.8 |
| E | NaOH (10%) | as required |

Phase C is combined with phase B and then phases A and B are separately heated to 75–80° C., cautiously brought together and homogenised. After cooling with slow stirring, the pH is adjusted to 7.0 using E.

Using an Optometrics SPF-290 Analyzer (2 $\mu$l/cm$^2$ on Transpore film) an in vitro SPF of 18 is determined. The Australian standard for UVA protection (Australian/New Zealand Standard, 15/NZS 2604: 1993) is met.

Example 6
Preparation of a W/O Emulsion

| INCI name | % w/w |
|---|---|
| PEG-30 dipolyhydroxy-stearate | 3.50 |
| PEG-22/dodecyl glycol copolymer | 1.50 |
| microcrystalline wax | 1.00 |
| hydrogenated castor oil | 1.00 |
| magnesium stearate | 1.00 |
| octyl stearate | 15.00 |
| coco glycerides | 2.00 |
| mineral oil | 3.00 |
| phenoxyethanols and (methyl, ethyl, propyl, butyl) parabens | 1.00 |
| octyl methoxycinnamate | 5.00 |
| dimethicone | 0.10 |
| deionised water | 49.90 |
| allantoin | 0.10 |
| magnesium sulfate | 1.00 |

| INCI name | % w/w |
|---|---|
| compound of formula (102) | 5.00 |
| propylene glycols | 4.00 |
| methylene bis-benzotriazolyl tetramethylbutytphenol (pH 5.5) | 6.00 |

The oil phase and the water phase are separately heated to 75–80° C. and cautiously brought together. That is followed by intensive homogenisation and cooling to room temperature with gentle stirring. Methylene bis-benzotriazolyl tetramethylbutylphenol is mixed into the emulsion obtained, with stirring.

Using an Optometrics SPF-290 Analyzer (2 $\mu$l/cm$^2$ on Transpore film) an in vitro SPF of 24 is determined.

Example 7
Preparation of a W/O Emulsion

| INCI name | formulation (A) % | formulation (B) % |
|---|---|---|
| methoxy PEG-22/dodecyl glycol copolymer | 3.00 | 3.00 |
| PEG-22/dodecyl glycol copolymer | 3.00 | 3.00 |
| hydroxyoctacosanyl hydroxystrearate | 3.00 | 3.00 |
| octyl stearate | 15.00 | 15.00 |
| coco glycerides | 2.00 | 2.00 |
| mineral oil | 3.00 | 3.00 |
| phenoxyethanols and (methyl, ethyl, propyl, butyl) parabens | 1.00 | 1.00 |
| octyl methoxycinnamate | 4.00 | 5.00 |
| dimethicone | 0.20 | 0.10 |
| deionised water | 47.70 | 43.80 |
| allantoin | 0.10 | 0.10 |
| compound of formula (102) | 5.00 | 4.00 |
| magnesium sulfate | 1.00 | 1.00 |
| propylene glycols | 4.00 | 4.00 |
| methylene bis-benzotriazolyl tetra-methylbutylphenol (pH 5.5) (50% suspension) | 8.00 | 12.00 |

The oil phase and the aqueous phase are separately heated to 75–80° C. and cautiously brought together. That is followed by intensive homogenisation and cooling to room temperature with gentle stirring. Methylene bis-benzotriazolyl tetramethylbutylphenol is added to the emulsion obtained, with stirring.

Using an Optometrics SPF-290 Analyzer (2 $\mu$l/cm$^2$ on Transpore film) in vitro SPF values of 20 (A) and 28 (B) are determined. The Australian standard for UVA protection (Australian/New Zealand Standard, 15/NZS 2604: 1993) is met.

What is claimed is:

1. A method of protecting ultraviolet-sensitive organic materials against the damaging action of UV radiation, which comprises applying thereto an effective protective amount of an indoline compound of the formula (1)

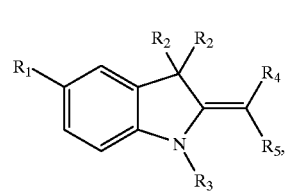

wherein $R_1$ is hydrogen; $C_1$–$C_5$alkyl; $C_1$–$C_{18}$alkoxy; or halogen;

$R_2$ is $C_1$–$C_8$alkyl; $C_5$–$C_7$cycloalkyl; $C_6$–$C_{10}$aryl;

$R_3$ is $C_1$–$C_{18}$alkyl; or a radical of the formula (1a)

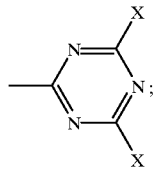

$R_4$ is hydrogen; or a radical of the formula (1b)

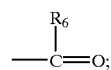

$R_5$ is a radical of formula (1c)

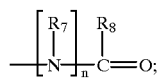

$C_1$–$C_{18}$alkoxy; or a radical of the formula (1d)

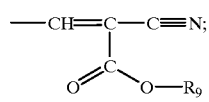

$R_6$ and $R_7$ are each independently of the other hydrogen; or $C_1$–$C_5$alkyl;

$R_8$ is hydrogen; $C_1$–$C_5$alkyl; $C_5$–$C_7$cycloalkyl; phenyl or phenyl-$C_1$–$C_3$alkyl;

$R_9$ is $C_1$–$C_{18}$alkyl;

X is halogen; a radical of formula (1e)

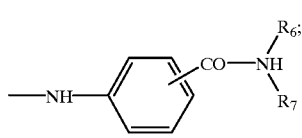

or (1f)

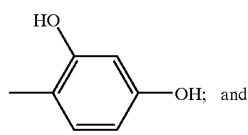

n is 0; or 1.

2. A method according to claim 1, wherein, in formula (1), $R_5$ is a radical of the formula (1g)

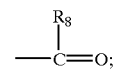

and $R_8$ is hydrogen; $C_1$–$C_5$alkyl; or phenyl.

3. A method according to claim 1, wherein $R_8$ is hydrogen or methyl.

4. A method according to claim 1, wherein $R_5$ is $C_1$–$C_{18}$alkoxy.

5. A method according to claim 1, wherein $R_5$ is a radical of the formula (1h)

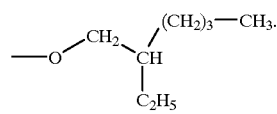

6. A method according to claim 1, wherein $R_5$ is a radical of formula (1i)

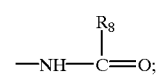

and $R_8$ is hydrogen; or methyl.

7. A method according to claim 1, wherein $R_3$ is $C_3$–$C_{18}$isoalkyl.

8. A method according to claim 1, which protects human and animal hair and the skin against the damaging action of UV radiation.

9. A cosmetic composition comprising from 0.1 to 15% by weight, based on the total weight of the composition, of a compound of the formula (1)

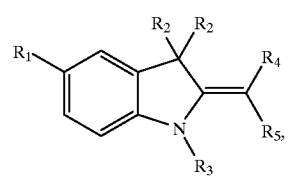

wherein $R_1$ is hydrogen; $C_1$–$C_5$alkyl; $C_1$–$C_{18}$alkoxy; or halogen;

$R_2$ is $C_1$–$C_8$alkyl; $C_5$–$C_7$cycloalkyl; $C_6$–$C_{10}$aryl;

$R_3$ is $C_1$–$C_{18}$alkyl; or a radical of the formula

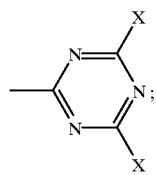
(1a)

$R_4$ is hydrogen; or a radical of the formula

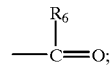
(1b)

$R_5$ is a radical of the formula

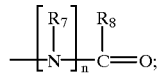
(1c)

$C_1$–$C_{18}$alkoxy; or a radical of the formula

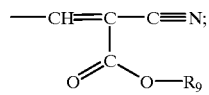
(1d)

$R_6$ and $R_7$ are each independently of the other hydrogen; or $C_1$–$C_5$alkyl;

$R_8$ is hydrogen; $C_1$–$C_5$alkyl; $C_5$–$C_7$cycloalkyl; phenyl; phenyl-$C_1$–$C_3$alkyl;

$R_9$ is $C_1$–$C_{18}$alkyl;

X is halogen; a radical of the formula

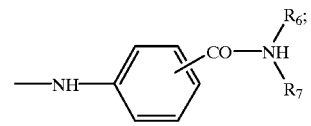
(1e)

or

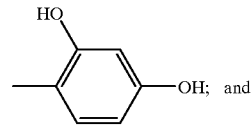
(1f)

n is 0; or 1, together with a cosmetically tolerable carrier or adjuvant.

10. A composition according to claim 9, which additionally comprises other UV-protective substances.

11. A composition according to claim 10, which comprises triazines, oxanilides, triazoles, vinyl-group-containing amides or cinnamic acid amides as other UV-protective substances.

* * * * *

UNITED STATES PATENT AND TRADEMARK OFFICE
CERTIFICATE OF CORRECTION

PATENT NO. : 6,358,496 B1
DATED : March 19, 2002
INVENTOR(S) : Rudolf Zink et al.

It is certified that error appears in the above-identified patent and that said Letters Patent is hereby corrected as shown below:

<u>Title page,</u>
Item [86], should read:
-- PCT No.: PCT/EP99/06984
§ 371 Date: Mar. 29, 2001
§ 102(e) Date: Mar. 29, 2001 --.

Signed and Sealed this

Twentieth Day of August, 2002

Attest:

JAMES E. ROGAN
Attesting Officer      *Director of the United States Patent and Trademark Office*